(12) United States Patent
Sakuta et al.

(10) Patent No.: US 11,007,127 B2
(45) Date of Patent: May 18, 2021

(54) BICONTINUOUS MICROEMULSION COMPOSITION AND COSMETIC

(71) Applicant: SHIN-ETSU CHEMICAL CO., LTD., Tokyo (JP)

(72) Inventors: Koji Sakuta, Annaka (JP); Takuya Abe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 123 days.

(21) Appl. No.: 16/189,479

(22) Filed: Nov. 13, 2018

(65) Prior Publication Data

US 2019/0159978 A1 May 30, 2019

(30) Foreign Application Priority Data

Nov. 29, 2017 (JP) .............................. JP2017-228794

(51) Int. Cl.

| | |
|---|---|
| *A61K 6/896* | (2020.01) |
| *A61K 8/06* | (2006.01) |
| *A61K 8/892* | (2006.01) |
| *A61Q 5/00* | (2006.01) |
| *A61K 8/31* | (2006.01) |
| *A61Q 5/12* | (2006.01) |
| *A61Q 19/10* | (2006.01) |
| *A61K 8/58* | (2006.01) |
| *A61K 8/37* | (2006.01) |
| *A61K 8/894* | (2006.01) |

(52) U.S. Cl.
CPC .............. *A61K 8/068* (2013.01); *A61K 8/066* (2013.01); *A61K 8/31* (2013.01); *A61K 8/37* (2013.01); *A61K 8/585* (2013.01); *A61K 8/892* (2013.01); *A61K 8/894* (2013.01); *A61Q 5/00* (2013.01); *A61Q 5/12* (2013.01); *A61Q 19/10* (2013.01); *A61K 2800/262* (2013.01)

(58) Field of Classification Search
None
See application file for complete search history.

(56) References Cited

U.S. PATENT DOCUMENTS

| | | | | |
|---|---|---|---|---|
| 5,412,004 | A * | 5/1995 | Tachibana ................. | A61K 8/06 514/844 |
| 5,705,562 | A | 1/1998 | Hill | |
| 9,289,372 | B2 * | 3/2016 | Sakuta .................... | A61K 8/894 |
| 2004/0136943 | A1 | 7/2004 | Tomokuni | |
| 2004/0146472 | A1 | 7/2004 | Nakanishi | |
| 2008/0293603 | A1 | 11/2008 | Watanabe et al. | |
| 2008/0311060 | A1 | 12/2008 | Sakuta et al. | |
| 2009/0238781 | A1 | 9/2009 | Sakuta et al. | |
| 2012/0321576 | A1 | 12/2012 | Sugiyama et al. | |
| 2014/0142016 | A1 | 5/2014 | Tomokuni et al. | |

(Continued)

FOREIGN PATENT DOCUMENTS

| | | |
|---|---|---|
| EP | 2014701 A2 | 1/2009 |
| EP | 2103301 A1 | 9/2009 |

(Continued)

OTHER PUBLICATIONS

Watanabe, Kei, "Emulsion and Solubilization", J. Jpn. Soc. Colour Mater., 89 (4), pp. 135-138. 2006.
May 8, 2019 Extended European Search Report issued in European Patent Application No. 18206255.4.
Oct. 6, 2020 Office Action issued in Japanese Patent Application No. 2017-228794.
Feb. 25, 2021 Office Action issued in European Patent Application No. 18 206 255.4.

*Primary Examiner* — Susan T Tran
(74) *Attorney, Agent, or Firm* — Oliff PLC

(57) ABSTRACT

The present invention provides a bicontinuous microemulsion composition, including: (A) polyglycerin group-containing organo(poly)siloxane shown by the general formula (1):

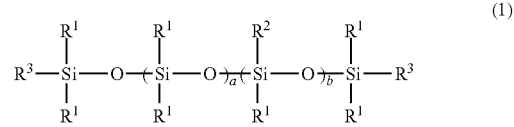

wherein $R^1$ represents an alkyl group or a phenyl group, $R^2$ represents a group having a polyglycerin structure shown by the formula (2) or the formula (3), $R^3$ represents $R^1$ or $R^2$, "a" is 0 to 6, "b" is 0 to 4, a+b is 0 to 10, and at least one of $R^3$ is $R^2$ when "b" is 0:

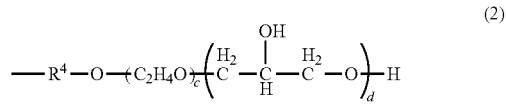

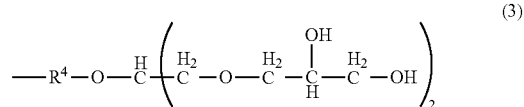

wherein $R^4$ represents an alkylene group or an aralkylene group, "c" is 0 to 10, and "d" is 2 to 6; (B) silicone oil having a viscosity of 20 mm²/s or less at 25° C., volatile hydrocarbon oil, or ester oil; and (C) water. This provide a transparent bicontinuous microemulsion composition in which anionic or cationic surfactant, and water-soluble monovalent or polyvalent alcohol are unnecessary; and a cosmetic with excellent pleasantness of use.

20 Claims, 2 Drawing Sheets

(56) References Cited

U.S. PATENT DOCUMENTS

| | | | |
|---|---|---|---|
| 2015/0335538 A1* | 11/2015 | Bernard | A61Q 1/14 424/401 |
| 2019/0077920 A1 | 3/2019 | Kamei | |
| 2019/0117531 A1 | 4/2019 | Nishida et al. | |

FOREIGN PATENT DOCUMENTS

| | | |
|---|---|---|
| JP | H04-020531 A | 1/1992 |
| JP | H09-183901 A | 7/1997 |
| JP | H10-316527 A | 12/1998 |
| JP | H11-293279 A | 10/1999 |
| JP | 2002-020791 A | 1/2002 |
| JP | 2002-179798 A | 6/2002 |
| JP | 2003/041664 A1 | 5/2003 |
| JP | 2003-146832 A | 5/2003 |
| JP | 2004-217640 A | 8/2004 |
| JP | 2005-097151 A | 4/2005 |
| JP | 2005-187355 A | 7/2005 |
| JP | 2005-194249 A | 7/2005 |
| JP | 2007-077302 A | 3/2007 |
| JP | 2009-196909 A | 9/2009 |
| JP | 2009-256616 A | 11/2009 |
| JP | 2010-222324 A | 10/2010 |
| JP | 2011-178769 A | 9/2011 |
| JP | 4776873 B2 | 9/2011 |
| JP | 2013-032348 A | 2/2013 |
| JP | 2014-224061 A | 12/2014 |
| JP | 2015-105255 A | 6/2015 |
| JP | 2017-066085 A | 4/2017 |
| JP | 2017-179317 A | 10/2017 |
| WO | 2017/187977 A1 | 11/2017 |

* cited by examiner

BICONTINUOUS MICROEMULSION COMPOSITION AND COSMETIC

TECHNICAL FIELD

The present invention relates to a bicontinuous microemulsion composition and a cosmetic containing the same.

BACKGROUND ART

Transparent microemulsion compositions composed of surfactant, oil, and water take on three types of form of water-continuous form, oil-continuous form, and bicontinuous form (NON-PATENT LITERATURE 1). Among them, the bicontinuous microemulsion compositions give cosmetics with improved functionality and pleasant to use, and large number of methods to obtain the composition have been reported.

They include, for example, compositions used for cleansing agents or cleaning agents of skin or hair (PATENT LITERATURES 1 to 7). In any of these compositions, however, a component of water-soluble alcohols is essential. In PATENT LITERATURE 5, hydrophilic surfactant and oleophilic surfactant are essential. In PATENT LITERATURES 7, 8, and 9, amphoteric surfactant and anionic surfactant are essential.

Although compositions in which water-soluble alcohol is unnecessary are described in PATENT LITERATURES 10 and 11, the former has an opaque appearance, and the latter is a composition with the water content of less than 5%, which has to be mixed so as to have a ratio of the composition:water of 4:6 when it is used.

They are reported to be applied as a sunblock composition other than the cleaning agent (PATENT LITERATURE 12). In bicontinuous microemulsion compositions, larger amount of surfactant is used than in the conventional oil-in-water type emulsion or water-in-oil type emulsion. Accordingly, use of silicone type surfactant is preferable in order to maintain light feeling when it is used as a cosmetic. PATENT LITERATURE 12 illustrates polyether modified silicone and polyglycerin modified silicone as an example of usable nonionic surfactant, but the specific structure is not suggested therein nor described in Examples.

The organopolysiloxane that contains a polyglycerin group (polyglycerin modified silicone) is disclosed in PATENT LITERATURES 13 to 19. However, any of them are used as surfactant to obtain water-in-oil type emulsion or oil-in-water type emulsion. These documents do not suggest the structure and composition required to obtain bicontinuous microemulsion.

CITATION LIST

Patent Literature

PATENT LITERATURE 1: Japanese Patent Laid-Open Publication (Kokai) No. 2009-196909
PATENT LITERATURE 2: Japanese Patent Laid-Open Publication (Kokai) No. 2015-105255
PATENT LITERATURE 3: Japanese Patent Laid-Open Publication (Kokai) No. 2017-66085
PATENT LITERATURE 4: Japanese Patent Laid-Open Publication (Kokai) No. 2004-217640
PATENT LITERATURE 5: Japanese Patent Laid-Open Publication (Kokai) No. 2013-32348
PATENT LITERATURE 6: Japanese Patent Laid-Open Publication (Kokai) No. 2014-224061
PATENT LITERATURE 7: Japanese Patent Laid-Open Publication (Kokai) No. 2010-222324
PATENT LITERATURE 8: Japanese Patent Laid-Open Publication (Kokai) No. 2007-77302
PATENT LITERATURE 9: Japanese Patent Laid-Open Publication (Kokai) No. 2002-20791
PATENT LITERATURE 10: Japanese Patent Laid-Open Publication (Kokai) No. 2005-187355
PATENT LITERATURE 11: Japanese Patent Laid-Open Publication (Kokai) No. 2005-194249
PATENT LITERATURE 12: Japanese Patent Laid-Open Publication (Kokai) No. 2011-178769
PATENT LITERATURE 13: Japanese Patent Laid-Open Publication (Kokai) No. H10-316527
PATENT LITERATURE 14: Japanese Patent Laid-Open Publication (Kokai) No. 2002-179798
PATENT LITERATURE 15: Japanese Patent Laid-Open Publication (Kokai) No. 2003-146832
PATENT LITERATURE 16: WO 2003/041664A1
PATENT LITERATURE 17: Japanese Patent Laid-Open Publication (Kokai) No. 2005-097151
PATENT LITERATURE 18: Japanese Patent Laid-Open Publication (Kokai) No. H11-293279
PATENT LITERATURE 19: Japanese Patent Laid-Open Publication (Kokai) No. 2009-256616

Non Patent Literature

NON PATENT LITERATURE 1: Kei Watanabe, J. Jpn. Soc. Colour Mater., 89(4), 135-138 (2016)

SUMMARY OF THE INVENTION

Technical Problem

The present invention was accomplished in view of the above-described problems. It is an object of the present invention to provide a transparent bicontinuous microemulsion composition in which anionic or cationic surfactant, and water-soluble monovalent or polyvalent alcohol are unnecessary, together with a cosmetic that has excellent pleasantness of use.

Solution to Problem

To solve the above problems, the present invention provides a bicontinuous microemulsion composition, comprising:

(A) polyglycerin group-containing organo(poly)siloxane shown by the following general formula (1):

wherein each $R^1$ independently represents an alkyl group having 1 to 10 carbon atoms or a phenyl group, $R^2$ represents a group having a polyglycerin structure shown by the following formula (2) or the following formula (3), each $R^3$ independently represents $R^4$ or $R^2$, "a" is a number of 0 to 6 and "b" is a number of 0 to 4 satisfying that a+b is 0 to 10, with the proviso that when "b" is 0, at least one of $R^3$ is $R^2$:

wherein R⁴ represents an alkylene group having 2 to 10 carbon atoms or an aralkylene group having 7 to 10 carbon atoms, "c" is a number of 0 to 10, and "d" is a number of 2 to 6;

(B) at least one kind of oil selected from the group consisting of silicone oils having a viscosity of 20 mm²/s or less at 25° C., volatile hydrocarbon oils, and ester oils; and (C) water.

In the bicontinuous microemulsion composition like this, (A) polyglycerin group-containing organo(poly)siloxane with a particular structure is effective as surfactant. Transparent bicontinuous microemulsion can be formed from only three components of this surfactant, (B) at least one kind of oil selected from silicone oils having a viscosity of 20 mm²/s or less at 25° C., volatile hydrocarbon oils, and ester oils, together with (C) water.

In the (A) polyglycerin group-containing organo(poly)siloxane, each R⁴ in the general formula (1) can independently represents an alkyl group having 1 to 5 carbon atoms.

The (A) polyglycerin group-containing organo(poly)siloxane like this is preferable since they can be easily synthesized.

In this case, the (A) polyglycerin group-containing organo (poly)siloxane can be shown by the general formula (1) in which R² is the same as described above, R³ is R², "a" is a number of 0 to 2 and "b" is 1 satisfying that a+b is 1 to 3, R⁴ in the formulae (2) and (3) is the same as described above, and the formula (2) is such that "c" is 0 and "d" is a number of 2 to 3; and the bicontinuous microemulsion composition can be oily.

Alternatively, the (A) polyglycerin group-containing organo(poly)siloxane can be shown by the general formula (1) in which R² and R³ are the same as described above, at least one of R³ is R², "a" is a number of 2 to 6 and "b" is 0 satisfying that a+b is 2 to 6, R⁴ in the formulae (2) and (3) is the same as described above, and the formula (2) is such that "c" is 0 and "d" is a number of 3 to 5; and the bicontinuous microemulsion composition can be oily.

Alternatively, the (A) polyglycerin group-containing organo(poly)siloxane can be shown by the general formula (1) in which R² is a group shown by the formula (2), R³ is R², "a" is a number of 0 to 1 and "b" is a number of 1 to 2 satisfying that a+b is 1 to 3, and the formula (2) is such that R⁴ is the same as described above, "c" is 0, and "d" is a number of 4 to 6; and the bicontinuous microemulsion composition can be aqueous.

Alternatively, the (A) polyglycerin group-containing organo(poly)siloxane can be shown by the general formula (1) in which R² is a group shown by the formula (2), R³ is R², "a" is a number of 0 to 2 and "b" is a number of 2 to 4 satisfying that a+b is 2 to 4, and the formula (2) is such that R⁴ is the same as described above, "c" is 0, and "d" is a number of 2 to 3; and the bicontinuous microemulsion composition can be aqueous.

Alternatively, the (A) polyglycerin group-containing organo(poly)siloxane can be shown by the general formula (1) in which R² and R³ are the same as described above, at least one of R³ is R², "a" is a number of 0 to 1 and "b" is a number of 0 to 1 satisfying that a+b is 0 to 2, R⁴ in the formulae (2) and (3) is the same as described above, and the formula (2) is such that "c" is 0 and "d" is a number of 3 to 6; and the bicontinuous microemulsion composition can be aqueous.

Alternatively, the (A) polyglycerin group-containing organo(poly)siloxane can be shown by the general formula (1) in which R² and R³ are the same as described above, "a" is a number of 0 to 3 and "b" is a number of 0 to 3 satisfying that a+b is 0 to 6, R⁴ in the formulae (2) and (3) is the same as described above, and the formula (2) is such that "c" is a number of 2 to 10 and "d" is a number of 2 to 6; and the bicontinuous microemulsion composition can be aqueous.

As described above, hydrophilic bicontinuous microemulsion and oleophilic bicontinuous microemulsion can be separately produced by selecting the structure of the (A) polyglycerin group-containing organo(poly)siloxane.

In this case, it is preferable that R¹ in the general formula (1) represent a methyl group in the (A) polyglycerin group-containing organo(poly)siloxane.

The (A) polyglycerin group-containing organo(poly)siloxane like this is preferable since they can be easily synthesized.

Alternatively, the (A) polyglycerin group-containing organo(poly)siloxane can be shown by the general formula (1) in which each R¹ independently represents an alkyl group having 6 to 10 carbon atoms or a phenyl group, R² is a group shown by the formula (2), R³ is R¹, "a" is a number of 0 to 2 and "b" is a number of 2 to 4 satisfying that a+b is 2 to 4, and the formula (2) is such that R⁴ is the same as described above, "c" is 0, and "d" is a number of 2 to 3; and the bicontinuous microemulsion composition can be oily.

As described above, it is possible to form oleophilic bicontinuous microemulsion by selecting a long chain alkyl group having 6 to 10 carbon atoms or a phenyl group as R¹ of the (A) polyglycerin group-containing organo (poly) siloxane.

The present invention also provides a cosmetic comprising the bicontinuous microemulsion composition described above.

The use of the inventive bicontinuous microemulsion composition makes the cosmetic to have excellent pleasantness of use.

Advantageous Effects of Invention

The inventive bicontinuous microemulsion composition can be obtained from only three components of the (A) polyglycerin group-containing organo(poly)siloxane with a particular structure, (B) at least one kind of oil selected from silicone oils having a viscosity of 20 mm²/s or less at 25° C., volatile hydrocarbon oils, and ester oils, and (C) water, without using water-soluble alcohols as an essential component. These three components can be mixed by a phase inversion temperature emulsification method or can be simply mixed and homogenously dispersed at room temperature to give bicontinuous microemulsion, which is easily prepared.

By adjusting the balance between the hydrophilicity and oleophilicity of the polyglycerin group-containing organo(poly)siloxane used as an activating agent, hydrophilic microemulsion and oleophilic microemulsion can be separately produced easily and can be selected in accordance with the objective cosmetics.

As described above, bicontinuous microemulsion compositions are frequently applied as a cleansing agent, and applied as a hydrophilic microemulsion in this case to be easily washed off after facial cleaning. The bicontinuous microemulsion composition in the present invention, using a highly detergent oil as the oil, is suitable for a cleansing agent. On the other hand, oleophilic bicontinuous microemulsion compositions have never been practically used for products. The inventive composition is useful as a cosmetic base not to be rinsed.

DESCRIPTION OF EMBODIMENTS

The present inventors diligently investigated to achieve the foregoing objects and consequently found that polyglycerin group-containing organo(poly)siloxane of particular structure with lower polymerization degree is effective as surfactant to find that transparent bicontinuous microemulsion can be obtained from only three components of this surfactant, at least one kind of oil selected from silicone oils having a viscosity of 20 mm²/s or less at 25° C., volatile hydrocarbon oils, and ester oils, together with water.

The present inventors also found that hydrophilic bicontinuous microemulsion and oleophilic bicontinuous microemulsion can be separately produced by selecting the structure of this surfactant; thereby bringing the present invention to completion.

That is, the present invention provides the following bicontinuous microemulsion composition and a cosmetic using the same emulsion composition.

The bicontinuous microemulsion composition of the present invention is a bicontinuous microemulsion composition, comprising:

(A) polyglycerin group-containing organo(poly)siloxane shown by the following general formula (1):

(1)

wherein each $R^1$ independently represents an alkyl group having 1 to 10 carbon atoms or a phenyl group, $R^2$ represents a group having a polyglycerin structure shown by the following formula (2) or the following formula (3), each $R^3$ independently represents $R^1$ or $R^2$, "a" is a number of 0 to 6 and "b" is a number of 0 to 4 satisfying that a+b is 0 to 10, with the proviso that when "b" is 0, at least one of $R^3$ is $R^2$:

(2)

(3)

wherein $R^4$ represents an alkylene group having 2 to 10 carbon atoms or an aralkylene group having 7 to 10 carbon atoms, "c" is a number of 0 to 10, and "d" is a number of 2 to 6;

(B) at least one kind of oil selected from the group consisting of silicone oils having a viscosity of 20 mm²/s or less at 25° C., volatile hydrocarbon oils, and ester oils; and

(C) water.

Hereinafter, the present invention will be more specifically described.

The component (A) used in the present invention is polyglycerin group-containing organo(poly)siloxane shown by the following general formula (1).

(1)

In the above formula (1), each $R^1$ independently represents an alkyl group having 1 to 10 carbon atoms or a phenyl group, $R^2$ represents a group shown by the following formula (2) or the following formula (3), each $R^3$ independently represents $R^4$ or $R^2$, at least one of $R^3$ is $R^2$ when "b" is 0, "a" is a number of 0 to 6 and "b" is a number of 0 to 4 satisfying that a+b is 0 to 10.

(2)

(3)

In the formula, $R^4$ represents an alkylene group having 2 to 10 carbon atoms or an aralkylene group having 7 to 10 carbon atoms, "c" is a number of 0 to 10, and "d" is a number of 2 to 6.

The alkyl group having 1 to 10 carbon atoms may be linear, branched, or cyclic, and is preferably a linear alkyl group. Illustrative examples thereof include a methyl group, an ethyl group, a propyl group, a butyl group, a pentyl group, a hexyl group, a heptyl group, an octyl group, a nonyl group, and a decyl group. The preferable example is a methyl group and an ethyl group.

In the formula (2), $R^4$ represents an alkylene group having 2 to 10 carbon atoms or an aralkylene group having 7 to 10 carbon atoms, "c" is a number of 0 to 10, and "d" is a number of 2 to 6. Illustrative examples of the alkylene group include a linear or branched alkylene group, such as an ethylene group, a propylene group, a trimethylene group, an n-butylene group, an isobutylene group, an s-butylene group, an n-octylene group, a 2-ethylhexylene group, and an n-decylene group; and illustrative examples of the aralkylene group includes a phenylenepropylene group, etc. Preferable examples are a propylene group, an n-butylene group, and an isobutylene group.

The polyglycerin group-containing organo(poly)siloxane with lower polymerization degree shown by the formula (1) like this, together with at least one kind of oil selected from silicone oils having a viscosity of 20 mm$^2$/s or less at 25° C., volatile hydrocarbon oils, and ester oils as well as water, makes it possible to form transparent bicontinuous microemulsion from only these three components.

The polyglycerin group-containing organo(poly)siloxane shown by the above formula (1) can be obtained by addition reaction of organohydrogenpolysiloxane shown by the following formula (4) and terminal unsaturated group-containing polyglycerin compound shown by the following formula (5) or the following formula (6).

In the above formulae, $R^1$, "a", "b", "c", and "d" have the same meanings as described above; $R^5$ is $R^1$ or a hydrogen atom; $R^6$ is a hydrogen atom or a methyl group; and $R^7$ is an alkylene group having 0 to 8 carbon atoms when $R^6$ is a hydrogen atom, and is an alkylene group having 0 to 7 carbon atoms when $R^6$ is a methyl group.

The terminal unsaturated group-containing polyglycerin compound shown by the formula (5) can also be obtained by monoalkenyl etherification of a polyglycerin compound, but it can be preferably obtained by addition reaction of a certain amount of glycidol to a terminal unsaturated group-containing alcohol compound shown by the following formula (7).

In the formula, $R^6$, $R^7$, and "c" have the same meanings as described above.

When the terminal unsaturated group is an allyl group and "c" is 0, the synthesis method thereof is described in JP 4776873B2. When the terminal unsaturated group is a group other than an allyl group and "c" is 1 to 10, it can be synthesized by the same method.

Incidentally, in the formula (2) and the formula (5), the polyglycerin unit is described as a structure in which glycidol is added only to the primary hydroxy group of the linear compound, that is, the compound of the formula (7). When one molecule of glycidol is added to the compound of the formula (7), however, a primary hydroxy group and a secondary hydroxy group are formed, which allows the second glycidol molecule to react to the secondary hydroxy group to form another component. The same applies to the case of reaction of the third and subsequent glycidol molecules. Accordingly, the polyglycerin units shown by the formula (2) and the formula (5) include not only linear ones but also ones partially having branched structure.

The polyglycerin group-containing organo(poly)siloxane obtained by addition reaction may be subjected to deodorant process by a conventional method, such as hydrolysis of the unreacted unsaturated terminal group with aqueous acidic solution and hydrogenation thereof.

The component (B) in the present invention is at least one kind of oil selected from the group consisting of silicone oils having a viscosity of 20 mm$^2$/s or less at 25° C., volatile hydrocarbon oils, and ester oils. The volatile oil preferably has a boiling point of 260° C. or less under 1 atmosphere.

The silicone oils having a viscosity of 20 mm$^2$/s or less at 25° C. may be any of linear, branched, and cyclic. Illustrative examples thereof include dimethylpolysiloxane, methylphenylpolysiloxane, and dimethylpolysiloxane with the methyl groups being partly substituted with an alkyl group(s) having 2 to 20 carbon atoms, and this oil may be volatile or not.

Among them, the ones that has a boiling point of 260° C. or less under 1 atmosphere are classified as volatile silicone. This volatile silicone oil may be any of linear, branched, and cyclic; and illustrative examples thereof include linear silicone oil, such as hexamethyldisiloxane, octamethyltrisiloxane, decamethyltetrasiloxane, dodecamethylpentasiloxane, heptamethylethyltrisiloxane, octamethyldiethyltetrasiloxane; branched silicone oil, such as tris(trimethylsiloxy)methylsilane and tetrakis(trimethylsiloxy)silane; and cyclic silicone oil, such as octamethylcyclotetrasiloxane, decamethylcyclopentasiloxane, dodecamethylcyclohexasiloxane, and tetramethyltetraethylcyclotetrasiloxane. Preferable examples include octamethyltrisiloxane, decamethyltetrasiloxane, dodecamethylpentasiloxane, tris(trimethylsiloxy)methylsilane, tetrakis(trimethylsiloxy)silane, decamethylcyclopentasiloxane, and dodecamethylcyclohexasiloxane.

As the oil, nonvolatile silicone oil having a viscosity of 20 mm$^2$/s or less at 25° C. is, when it is used, preferably combined with volatile silicone oil having a viscosity of 20 mm$^2$/s or less at 25° C. It is particularly preferable to use only volatile silicone oil having a viscosity of 20 mm$^2$/s or less at 25° C.

As the volatile hydrocarbon oil, isoparaffin hydrocarbons are exemplified, and illustrative examples thereof include Isoper C, E, G, H, L, and M (manufactured by Exxon, trade name); IP solvent 1016, 1620, and 2028 (manufactured by Idemitsu Petrochemical Co., Ltd., trade name); Shellsol MC311, MC421, and MC531 (manufactured by Shell Chemicals, trade name); Marukazol R (manufactured by MARUZEN PETROCHEMICAL CO., LTD., trade name); and Permethyl 99A and 101A (manufactured by EC Eldorchemie, trade name).

The ester oil is not particularly limited and may be the known ones used for cosmetics and is not necessarily volatile. Illustrative examples thereof include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, neopentyl glycol diethylhexanoate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, isononyl isononanate, isotridecyl isononanate, glyceryl triisooctanoate, glyceryl triisostearate, glyceryl triisopalmitate, glyceryl monostearate, glyceryl di-2-heptylundecanoate, glyceryl trimyristate, and diglyceryl myristate isostearate.

In the bicontinuous microemulsion composition of the present invention, the ratio of contents of each composition (A), (B), and (C) is not limited, but is preferably such that 10 to 500 parts by mass of the component (B) oil and 10 to 500 parts by mass of the component (C) water are contained relative to 100 parts by mass of the component (A) polyglycerin group-containing organo (poly) siloxane.

As a method for homogeneously disperse the components (A), (B), and (C), a phase inversion temperature emulsification method can be used. For example, it can be obtained such that the component (A) and the component (B) are mixed and heated to a prescribed temperature, followed by adding the component (C) that has been heated to the same temperature, these are mixed homogeneously, and the mixture is quenched. Alternatively, the three components may be mixed with the temperature being kept at the room temperature without being heated.

The bicontinuous microemulsion structure can be determined by observing an electron microscope image using a freeze-fracture replica technique of known method. More conveniently, it can be determined by solubility test of pigments. The solubility test of pigments is a method to add each of aqueous pigments and oily pigments to determine that it is amphiphilic when it is rapidly mixed with both of water and oil.

Whether the inventive bicontinuous microemulsion composition is aqueous or oily can be determined by the following method. When several drops of the microemulsion composition are rapidly dispersed homogeneously to excess water after being dropped thereto and are not dispersed to excess oil after being dropped thereto, it is aqueous. On the other hand, when they are rapidly dispersed homogeneously to excess oil after being dropped thereto and are not dispersed to excess water after being dropped thereto, it is oily.

One of the preferable embodiment of the present invention is an oily bicontinuous microemulsion composition composed of the component (A) polyglycerin group-containing organo(poly)siloxane shown by the formula (1) in which each $R^1$ independently represents an alkyl group having 1 to 5 carbon atoms, $R^2$ is the same as described above, $R^4$ in the formulae (2) and (3) is the same as described above, the formula (1) is such that $R^3$ is $R^1$, "a" is a number of 0 to 2 and "b" is 1 satisfying that a+b is 1 to 3, and the formula (2) is such that "c" is 0 and "d" is a number of 2 to 3; the component (B) oil; and the component (C) water. In this case, the ratio of contents is preferably such that 50 to 400 parts by mass of the component (B) and 50 to 300 parts by mass of the component (C) are contained relative to 100 parts by mass of the component (A).

One of the other preferable embodiments is an oily bicontinuous microemulsion composition composed of the component (A) polyglycerin group-containing organo(poly)siloxane shown by the formula (1) in which each $R^1$ independently represents an alkyl group having 1 to 5 carbon atoms, $R^2$ and $R^3$ are the same as described above, at least one of $R^3$ is $R^2$, $R^4$ in the formulae (2) and (3) is the same as described above, "a" is a number of 2 to 6 and "b" is 0 satisfying that a+b is 2 to 6, and the formula (2) is such that "c" is 0 and "d" is a number of 3 to 5; the component (B) oil; and the component (C) water. In this case, the ratio of contents is preferably such that 50 to 300 parts by mass of the component (B) and 10 to 100 parts by mass of the component (C) are contained relative to 100 parts by mass of the component (A).

One of the still other preferable embodiments is an aqueous bicontinuous microemulsion composition composed of the component (A) polyglycerin group-containing organo(poly)siloxane shown by the formula (1) in which each $R^4$ independently represents an alkyl group having 1 to 5 carbon atoms, $R^3$ is $R^4$, $R^2$ is a group shown by the formula (2), "a" is a number of 0 to 1 and "b" is a number of 1 to 2 satisfying that a+b is 1 to 3, "c" is 0, and "d" is a number of 4 to 6; the component (B) oil; and the component (C) water. In this case, the ratio of contents is preferably such that 50 to 400 parts by mass of the component (B) and 20 to 300 parts by mass of the component (C) are contained relative to 100 parts by mass of the component (A).

One of the still other preferable embodiments is an aqueous bicontinuous microemulsion composition composed of the component (A) polyglycerin group-containing organo(poly)siloxane shown by the formula (1) in which each $R^4$ independently represents an alkyl group having 1 to 5 carbon atoms, $R^3$ is $R^4$, $R^2$ is a group shown by the formula (2), $R^4$ in the formula (2) is the same as described above, "a" is a number of 0 to 2 and "b" is a number of 2 to 4 satisfying that a+b is 2 to 4, "c" is 0, and "d" is a number of 2 to 3; the component (B) oil; and the component (C) water. In this case, the ratio of contents is preferably such that 30 to 200 parts by mass of the component (B) and 50 to 400 parts by mass of the component (C) are contained relative to 100 parts by mass of the component (A).

One of the still other preferable embodiments is an aqueous bicontinuous microemulsion composition composed of the component (A) polyglycerin group-containing organo(poly)siloxane shown by the formula (1) in which each $R^1$ independently represents an alkyl group having 1 to 5 carbon atoms, $R^2$ and $R^3$ are the same as described above, at least one of $R^3$ is $R^2$, $R^4$ in the formulae (2) and (3) is the same as described above, "a" is a number of 0 to 1 and "b" is a number of 0 to 1 satisfying that a+b is 0 to 2, "c" is 0 and "d" is a number of 3 to 6; the component (B) oil; and the component (C) water. In this case, the ratio of contents is preferably such that 10 to 300 parts by mass of the component (B) and 50 to 300 parts by mass of the component (C) are contained relative to 100 parts by mass of the component (A).

One of the still other preferable embodiments is an aqueous bicontinuous microemulsion composition composed of the component (A) polyglycerin group-containing organo(poly)siloxane shown by the formula (1) in which each $R^1$ independently represents an alkyl group having 1 to 5 carbon atoms, $R^2$, $R^3$, and $R^4$ are the same as described above, "a" is a number of 0 to 3 and "b" is a number of 0 to 3 satisfying that a+b is 0 to 6, "c" is a number of 2 to 10 and "d" is a number of 2 to 6; the component (B) oil; and the component (C) water. In this case, the ratio of contents is preferably such that 50 to 200 parts by mass of the component (B) and 100 to 400 parts by mass of the component (C) are contained relative to 100 parts by mass of the component (A).

One of the still other preferable embodiments is an oily bicontinuous microemulsion composition composed of the component (A) polyglycerin group-containing organo(poly)siloxane shown by the formula (1) in which each $R^1$ independently represents an alkyl group having 6 to 10 carbon atoms or a phenyl group, $R^2$ is a group shown by the formula (2), $R^3$ is $R^1$, "a" is a number of 0 to 2 and "b" is a number of 2 to 4 satisfying that a+b is 2 to 4, and the formula (2) is such that $R^4$ is the same as described above, "c" is 0, and "d" is a number of 2 to 3; the component (B) oil; and the component (C) water. In this case, the ratio of contents is preferably such that 30 to 200 parts by mass of the component (B) and 50 to 400 parts by mass of the component (C) are contained relative to 100 parts by mass of the component (A).

As described above, an oily microemulsion composition and an aqueous microemulsion composition which are bicontinuous can be separately produced by selecting the structure of the polyglycerin group-containing organo (poly)siloxane.

The present invention further provides a cosmetic that contains the bicontinuous microemulsion composition described above. The cosmetic is not limited to particular types, and illustrative examples thereof include a cleansing agent, a skin care cosmetic, a hair care cosmetic, an antiperspirant cosmetic, a make-up cosmetic, and a UV-cut cosmetic.

Incidentally, in conventional cleansing agents, an oily component in an water-in-oil type emulsion composition tend to remain after being rinsed with water, and oil-in-water type emulsion composition tend to exhibit insufficient washing effect to oily components. The bicontinuous microemulsion composition, such as the present invention, can be used with the oleophilicity being kept sufficient in washing and is easily washed off in rinsing after washing.

When forming a cosmetic using the composition of the present invention, a known component(s) for cosmetics may be blended. Illustrative examples thereof include silicone oil having a viscosity more than 20 mm²/s at 25° C., nonvolatile hydrocarbon oil; lower alcohols, such as ethanol and 2-propanol; polyvalent alcohols, such as propylene glycol, butylene glycol, dibutylene glycol, and glycerin; higher alcohols, such as lauryl alcohol, myristyl alcohol, and stearyl alcohol; salts, such as inorganic salts, organic salts, and amine hydrochloride; vegetable polymers, such as arabia gum, guar gum, and starch; microorganism polymers, such as xanthane gum and dextrin; cellulose polymers, such as methyl cellulose, methylhydroxypropylcellulose, and carboxymethylcellulose; vinyl polymers, such as carboxyvinylpolymer; acrylic polymers, such as sodium polyacrylate and polyacryl amide; inorganic polymers, such as bentonite, montmorillonite, and silicic anhydride; water-soluble synthetic polymers, such as polyvinyl alcohol and polyoxyethylene; powders, such as inorganic powder, organic powder, metal salt powder, colored pigment, pearl pigment, and natural pigment; and other component used for ordinal cosmetics, such as nonionic surfactant other than the inventive polyglycerin group-containing organo(poly)siloxane, cationic surfactant, anionic surfactant, an ultraviolet light protective agent, an antiperspirant, an oil-soluble gelation agent, a moisturizer, an antioxidant, a perfume (fragrance), an antiseptic, a pH controller, a refrigerant, a skin-whitening agent, and vitamins.

EXAMPLES

Hereinafter, the present invention will be explained more specifically by showing Synthesis Examples and Examples, but the present invention is not limited to the following Examples.

Synthesis Example 1

Into a flask, 250.0 g of 1,1,1,3,5,5,5-heptamethyltrisiloxane, 344.0 g of the following polyglycerin compound [A] (degree of unsaturation: 3.41 meq/g), and 891.0 g of 2-propanol were introduced. To this, 0.06 g of Karstedt catalyst (platinum concentration: 3%) and 0.12 g of 10% potassium acetate solution in ethanol were added, and the reaction was carried out at 80° C. for 5 hours. After the reaction, the solvent was removed under reduced pressure to give the following polyglycerin-modified silicone (hereinafter referred to as Compound 1).

Synthesis Example 2

Into a flask, 40.0 g of 1,1,1,3,5,5,5-heptamethyltrisiloxane, 76.0 g of the following polyglycerin compound [B] (degree of unsaturation: 2.47 meq/g), and 174.0 g of 2-propanol were introduced. To this, 0.012 g of Karstedt catalyst (platinum concentration: 3%) and 0.024 g of 10% potassium acetate solution in ethanol were added to give the following polyglycerin-modified silicone (hereinafter referred to as Compound 2) as in Synthesis Example 1.

Synthesis Example 3

Into a flask, 30.0 g of 1,1,1,3,5,5,5-heptamethyltrisiloxane, 62.3 g of the following polyglycerin compound [C] (degree of unsaturation: 2.26 meq/g),

[C]

and 138.5 g of 2-propanol were introduced. To this, 0.009 g of Karstedt catalyst (platinum concentration: 3%) and 0.018 g of 10% potassium acetate solution in ethanol were added to give the following polyglycerin-modified silicone (hereinafter referred to as Compound 3) as in Synthesis Example 1.

Synthesis Example 4

Into a flask, 20.0 g of 1,1,1,3,5,7,7,7-octamethyltetrasiloxane, 49.7 g of the polyglycerin compound [A] described above, and 104.6 g of 2-propanol were introduced. To this, 0.007 g of Karstedt catalyst (platinum concentration: 3%) and 0.014 g of 10% potassium acetate solution in ethanol were added to give the following polyglycerin-modified silicone (hereinafter referred to as Compound 4) as in Synthesis Example 1.

Synthesis Example 5

Into a flask, 25.0 g of 1,1,1,3,3-pentamethyldisiloxane, 55.2 g of the polyglycerin compound [A] described above, and 120.0 g of 2-propanol were introduced. To this, 0.008 g of Karstedt catalyst (platinum concentration: 3%) and 0.016 g of 10% potassium acetate solution in ethanol were added to give the following polyglycerin-modified silicone (hereinafter referred to as Compound 5) as in Synthesis Example 1.

Synthesis Example 6

Into a flask, 250 g of 1,1,1,3,5,5,5-heptamethyltrisiloxane, 347.6 g of the following polyglycerin compound [D] (degree of unsaturation: 3.40 meq/g),

[D]

and 891.0 g of 2-propanol were introduced. To this, 0.06 g of Karstedt catalyst (platinum concentration: 3%) and 0.12 g of 10% potassium acetate solution in ethanol were added to give the following polyglycerin-modified silicone (hereinafter referred to as Compound 6) as in Synthesis Example 1.

Synthesis Example 7

Into a flask, 250 g of 1,1,1,3,5,5,5-heptamethyltrisiloxane, 364.2 g of the following polyglycerin compound [E] (degree of unsaturation: 3.25 meq/g),

[E]

and 891.0 g of 2-propanol were introduced. To this, 0.06 g of Karstedt catalyst (platinum concentration: 3%) and 0.12 g of 10% potassium acetate solution in ethanol were added to give the following polyglycerin-modified silicone (hereinafter referred to as Compound 7) as in Synthesis Example 1.

Synthesis Example 8

Into a flask, 15.0 g of 1,1,1,3,5,5,5-heptamethyltrisiloxane, 32.9 g of the following polyglycerin compound [F] (degree of unsaturation: 2.14 meq/g),

[F]

and 71.9 g of 2-propanol were introduced. To this, 0.006 g of Karstedt catalyst (platinum concentration: 3%) and 0.012 g of 10% potassium acetate solution in ethanol were added to give the following polyglycerin-modified silicone (hereinafter referred to as Compound 8) as in Synthesis Example 1.

Synthesis Example 9

Into a flask, 12.5 g of 1,1,1,3,5,5,5-heptamethyltrisiloxane, 32.6 g of the following polyglycerin compound [G] (degree of unsaturation: 1.80 meq/g), and 90.2 g of 2-propanol were introduced. To this, 0.006 g of Karstedt catalyst (platinum concentration: 3%) and 0.012 g of 10% potassium acetate solution in ethanol were added to give the following polyglycerin-modified silicone (hereinafter referred to as Compound 9) as in Synthesis Example 1.

Synthesis Example 10

Into a flask, 30.0 g of the following organohydrogenpolysiloxane [H], 36.7 g of the polyglycerin compound [A] described above, and 100.0 g of 2-propanol were introduced. To this, 0.007 g of Karstedt catalyst (platinum concentration: 3%) and 0.014 g of 10% potassium acetate solution in ethanol were added to give the following polyglycerin-modified silicone (hereinafter referred to as Compound 10) as in Synthesis Example 1.

Examples 1 to 38

In accordance with compositions shown in Tables 1 to 10, each of the polyglycerin-modified silicones obtained in Synthesis Examples 1 to 10, oil (decamethylcyclopentasiloxane: D5, silicone oil described below, isododecane, or ester oil described below), and water were mixed at the room temperature to prepare emulsion. The formulation amount is shown in mass %. Incidentally, the appearance of the emulsion is judged visually. In the pigment solubility test, the water solubility was investigated by adding aqueous water-soluble pigment (Blue #1) solution (concentration: 1.0 mass %) to the obtained emulsion. The oil solubility was similarly investigated by adding oil-soluble pigment (β-carotene) solution in decamethylcyclopentasiloxane (concentration: 1.0 mass %). The water dispersibility was investigated by adding one drop of the emulsion to 10 ml of water. The oil dispersibility was investigated by adding one drop of the emulsion to 10 ml of D5.

TABLE 1

| | | Example 1 | Example 2 | Example 3 |
|---|---|---|---|---|
| Formulated composition | Compound 1 | 25 | 20 | 20 |
| | D5 | 25 | 65 | 55 |
| | water | 50 | 15 | 25 |
| Appearance of emulsion | | Colorless, transparent | Colorless, transparent | Colorless, transparent |
| pigment solubility test | Water solubility | Homogeneously dissolved | Homogeneously dissolved | Homogeneously dissolved |
| | Oil solubility | Homogeneously dissolved | Homogeneously dissolved | Homogeneously dissolved |
| Water dispersibility | | Separated | Separated | Separated |
| Oil dispersibility | | Homogeneously dispersed | Homogeneously dispersed | Homogeneously dispersed |

TABLE 2

|  |  | Example 4 | Example 5 | Example 6 | Example 7 |
|---|---|---|---|---|---|
| Formulated composition | Compound 2 | 25 | 25 | 36 | 30 |
|  | D5 | 25 | 12.5 | 50 | 45 |
|  | Silicone oil[*1] | 0 | 12.5 | 0 | 0 |
|  | isododecane | 0 | 0 | 0 | 0 |
|  | water | 50 | 50 | 14 | 25 |
| Appearance of emulsion |  | Colorless, transparent | Colorless, transparent | Colorless, transparent | Colorless, transparent |
| pigment solubility test | Water solubility | Homogeneously dissolved | Homogeneously dissolved | Homogeneously dissolved | Homogeneously dissolved |
|  | Oil solubility | Homogeneously dissolved | Homogeneously dissolved | Homogeneously dissolved | Homogeneously dissolved |
| Water dispersibility |  | Homogeneously dispersed | Homogeneously dispersed | Homogeneously dispersed | Homogeneously dispersed |
| Oil dispersibility |  | Separated | Separated | Separated | Separated |
|  |  | Example 8 | Example 9 | Example 10 | Example 11 |
| Formulated composition | Compound 2 | 30 | 25 | 35 | 25.0 |
|  | D5 | 40 | 20 | 20 | 0 |
|  | Silicone oil[*1] | 0 | 5 | 5 | 12.5 |
|  | isododecane | 0 | 0 | 0 | 12.5 |
|  | water | 30 | 50 | 40 | 50.0 |
| Appearance of emulsion |  | Colorless, transparent | Colorless, transparent | Colorless, transparent | Colorless, transparent |
| pigment solubility test | Water solubility | Homogeneously dissolved | Homogeneously dissolved | Homogeneously dissolved | Homogeneously dissolved |
|  | Oil solubility | Homogeneously dissolved | Homogeneously dissolved | Homogeneously dissolved | Homogeneously dissolved |
| Water dispersibility |  | Homogeneously dispersed | Homogeneously dispersed | Homogeneously dispersed | Homogeneously dispersed |
| Oil dispersibility |  | Separated | Separated | Separated | Separated |

[*1]Silicone oil: dimethylpolysiloxane with the viscosity of 6 $mm^2/s$ at 25° C.

TABLE 3

|  |  | Example 12 | Example 13 | Example 14 |
|---|---|---|---|---|
| Formulated composition | Compound 3 | 28 | 25 | 20 |
|  | D5 | 28 | 25 | 20 |
|  | water | 44 | 50 | 60 |
| Appearance of emulsion |  | Colorless, transparent | Colorless, transparent | Colorless, transparent |
| pigment solubility test | Water solubility | Homogeneously dissolved | Homogeneously dissolved | Homogeneously dissolved |
|  | Oil solubility | Homogeneously dissolved | Homogeneously dissolved | Homogeneously dissolved |
| Water dispersibility |  | Homogeneously dispersed | Homogeneously dispersed | Homogeneously dispersed |
| Oil dispersibility |  | Separated | Separated | Separated |

TABLE 4

|  |  | Example 15 | Example 16 | Example 17 |
|---|---|---|---|---|
| Formulated composition | Compound 4 | 25 | 25 | 20 |
|  | D5 | 25 | 15 | 20 |
|  | water | 50 | 60 | 60 |
| Appearance of emulsion |  | Colorless, transparent | Colorless, transparent | Colorless, transparent |
| pigment solubility test | Water solubility | Homogeneously dissolved | Homogeneously dissolved | Homogeneously dissolved |
|  | Oil solubility | Homogeneously dissolved | Homogeneously dissolved | Homogeneously dissolved |
| Water dispersibility |  | Homogeneously dispersed | Homogeneously dispersed | Homogeneously dispersed |
| Oil dispersibility |  | Separated | Separated | Separated |

TABLE 5

| Formulated composition | | Example 18 | Example 19 | Example 20 | Example 21 | Example 22 |
|---|---|---|---|---|---|---|
| | Compound 5 | 40 | 35 | 35 | 35 | 25 |
| | D5 | 15 | 15 | 5 | 15 | 50 |
| | water | 45 | 50 | 60 | 50 | 25 |
| Appearance of emulsion | | Colorless, transparent | Colorless, transparent | Colorless, transparent | Colorless, transparent | Colorless, transparent |
| pigment solubility test | Water solubility | Homogeneously dissolved | Homogeneously dissolved | Homogeneously dissolved | Homogeneously dissolved | Homogeneously dissolved |
| | Oil solubility | Homogeneously dissolved | Homogeneously dissolved | Homogeneously dissolved | Homogeneously dissolved | Homogeneously dissolved |
| Water dispersibility | | Homogeneously dispersed | Homogeneously dispersed | Homogeneously dispersed | Homogeneously dispersed | Homogeneously dispersed |
| Oil dispersibility | | Separated | Separated | Separated | Separated | Separated |

TABLE 6

| | | Example 23 | Example 24 | Example 25 |
|---|---|---|---|---|
| Formulated composition | Compound 6 | 25 | 20 | 20 |
| | D5 | 25 | 65 | 55 |
| | water | 50 | 15 | 25 |
| Appearance of emulsion | | Colorless, transparent | Colorless, transparent | Colorless, transparent |
| pigment solubility test | Water solubility | Homogeneously dissolved | Homogeneously dissolved | Homogeneously dissolved |
| | Oil solubility | Homogeneously dissolved | Homogeneously dissolved | Homogeneously dissolved |
| Water dispersibility | | Separated | Separated | Separated |
| Oil dispersibility | | Homogeneously dispersed | Homogeneously dispersed | Homogeneously dispersed |

TABLE 7

| | | Example 26 | Example 27 | Example 28 |
|---|---|---|---|---|
| Formulated composition | Compound 7 | 25 | 20 | 20 |
| | D5 | 25 | 65 | 55 |
| | water | 50 | 15 | 25 |
| Appearance of emulsion | | Colorless, transparent | Colorless, transparent | Colorless, transparent |
| pigment solubility test | Water solubility | Homogeneously dissolved | Homogeneously dissolved | Homogeneously dissolved |
| | Oil solubility | Homogeneously dissolved | Homogeneously dissolved | Homogeneously dissolved |
| Water dispersibility | | Separated | Separated | Separated |
| Oil dispersibility | | Homogeneously dispersed | Homogeneously dispersed | Homogeneously dispersed |

TABLE 8

| | | Example 29 | Example 30 | Example 31 | Example 32 |
|---|---|---|---|---|---|
| Formulated composition | Compound 8 | 25 | — | — | — |
| | Compound 9 | — | 25 | — | — |
| | Compound 10 | — | — | 25 | 25 |
| | D5 | 37.5 | 67.5 | 25 | 15 |
| | water | 37.5 | 7.5 | 50 | 60 |
| Appearance of emulsion | | Colorless, transparent | Colorless, transparent | Colorless, transparent | Colorless, transparent |
| pigment solubility test | Water solubility | Homogeneously dissolved | Homogeneously dissolved | Homogeneously dissolved | Homogeneously dissolved |
| | Oil solubility | Homogeneously dissolved | Homogeneously dissolved | Homogeneously dissolved | Homogeneously dissolved |
| Water dispersibility | | Homogeneously dispersed | Homogeneously dispersed | Separated | Separated |
| Oil dispersibility | | Separated | Separated | Homogeneously dispersed | Homogeneously dispersed |

TABLE 9

|  |  | Example 33 | Example 34 | Example 35 | Example 36 |
|---|---|---|---|---|---|
| Formulated composition | Compound 10 | 25 | 25 | 35 | 25 |
|  | D5 | 12.5 | 25 | — | — |
|  | Ester oil*[2] | 12.5 | 25 | — | — |
|  | isododecane | — | — | 25 | 50 |
|  | water | 50 | 25 | 40 | 25 |
| Appearance of emulsion |  | Colorless, transparent | Colorless, transparent | Colorless, transparent | Colorless, transparent |
| pigment solubility test | Water solubility | Homogeneously dissolved | Homogeneously dissolved | Homogeneously dissolved | Homogeneously dissolved |
|  | Oil solubility | Homogeneously dissolved | Homogeneously dissolved | Homogeneously dissolved | Homogeneously dissolved |
| Water dispersibility |  | Separated | Separated | Separated | Separated |
| Oil dispersibility |  | Homogeneously dispersed | Homogeneously dispersed | Homogeneously dispersed | Homogeneously dispersed |

*[2]Ester oil: 2-ethylhexyl palmitate

TABLE 10

|  |  | Example 37 | Example 38 |
|---|---|---|---|
| Formulated composition | Compound 2 | 35 | — |
|  | Compound 1 | — | 35 |
|  | isododecane | 35 | 35 |
|  | water | 30 | 30 |
| Appearance of emulsion |  | Colorless, transparent | Colorless, transparent |
| pigment solubility test | Water solubility | Homogeneously dissolved | Homogeneously dissolved |
|  | Oil solubility | Homogeneously dissolved | Homogeneously dissolved |
| Water dispersibility |  | Homogeneously dispersed | Separated |
| Oil dispersibility |  | Separated | Homogeneously dispersed |

As described in Tables 1 to 10 described above, in Examples 1 to 38, both of the water-soluble pigment and the oil-soluble pigment were homogeneously dissolved in the pigment solubility test, which confirmed that the obtained emulsion had a bicontinuous structure.

Figure 1:
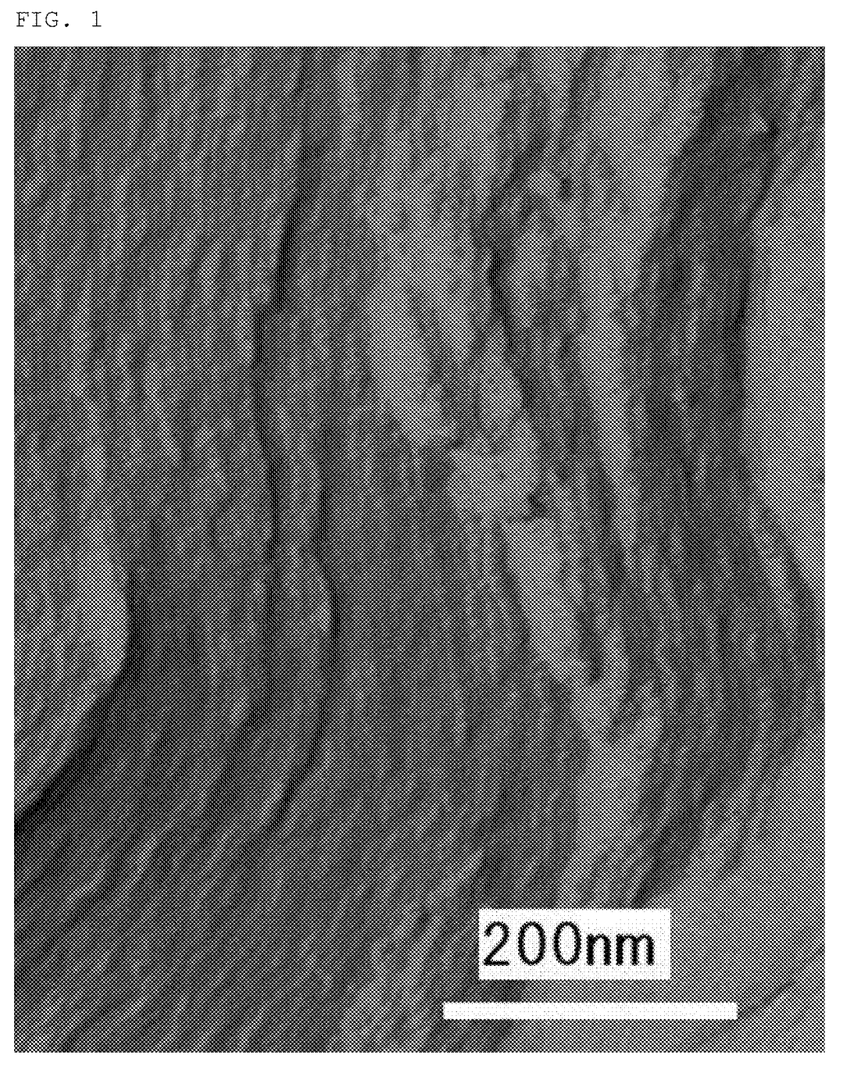
FIG. 1 is a photograph of an electron microscope image of microemulsion obtained in Example 4, using a freeze-fracture replica technique.

The emulsion obtained in Example 4 was observed through electron microscope (manufactured by JEOL Ltd., transmission electron microscope JEM-1010) using a freeze-fracture replica technique. The result is shown in FIG. 1. It was confirmed that this emulsion, having a layered structure, was a bicontinuous microemulsion.

Examples 39 to 42

Each of the compositions obtained in Examples 4, 5, 13, and 37 was used as a cleansing agent to confirm the effect. The evaluation method was as follows: 0.1 g of commercially available liquid foundation (manufactured by Shiseido Company, Limited, MAQuillAGE true liquid long keep UV) was applied to an arm of a panelist, and 1 hour later, the arm was massaged for 10 times with 1 g of the composition for cleansing under a constant force and speed, washed with running water, and evaluated according to the following standards.

(Cleansing Efficiency)

Excellent: sufficiently came off

Fair: partly remained

Bad: remained (Easiness in Washing)

Excellent: immediately washed

Good: washed without a problem

Bad: washing required loner time

TABLE 11

|  | Example 39 | Example 40 | Example 41 | Example 42 |
|---|---|---|---|---|
| Cleansing agent | Composition of Example 4 | Composition of Example 5 | Composition of Example 13 | Composition of Example 37 |
| Cleansing efficiency | Excellent | Excellent | Excellent | Excellent |
| Easiness in washing | Excellent | Excellent | Excellent | Excellent |

Example 43

The emulsion of the following composition was prepared and was used for a hair protective agent. The pigment solubility test and dispersibility test were carried out in the same manner as described above.

TABLE 12

|  |  | Component | Formulated amount (mass %) |
|---|---|---|---|
| Hair protective composition | Emulsion | Compound 1 synthesized in Synthesis Example 1 | 25.0 |
|  |  | D5 | 25.0 |
|  |  | water | 33.0 |
|  | Highly viscous polyether-modified silicone*[3] |  | 10.0 |
|  | ethanol |  | 7.0 |
| Appearance pigment solubility test | Water solubility |  | Colorless, transparent Homogeneously dissolved |
|  | Oil solubility |  | Homogeneously dissolved |

TABLE 12-continued

| Component | Formulated amount (mass %) |
|---|---|
| Water dispersibility | Separated |
| Oil dispersibility | Homogeneously dispersed |

*[3]highly viscous polyether-modified silicone having the following structure (viscosity: 421000 mPa · s at 25° C.)

In the pigment solubility test, both of the water-soluble pigment and the oil-soluble pigment were homogeneously dissolved, which confirmed that the obtained emulsion had a bicontinuous structure.

Subsequently, using this hair protective agent, the efficiency of protecting a hair was confirmed by the following method.
(Treating Method of Hair)
1. About 1.5 g of commercially available hairs (ordinal hairs) were tied on each one end to prepare a hair bundle, and this was observed through electron microscope and photographed (before treatment).
2. The hair bundle was introduced into a vessel containing solution of a protective agent and was soaked for 5 minutes.
3. The hair bundle was taken out, and the excess liquid attached thereto was wiped out. Then, the hair bundle was dried being hung with the hair end pointing downward. After drying, the hair bundle was observed through electron microscope and photographed (after treatment).
4. The hair bundle was introduced into solution of commercially available non-silicone shampoo and wad washed for 5 minutes with shaking. After the shampoo, components were rinsed, the excess water drops were wiped out with a towel. Then, the hair bundle was dried being hung with the hair end pointing downward. After drying, the hair bundle was observed through electron microscope and photographed (after shampoo).
(Conditions for Observing and Taking Electron Microscope Photograph)
(Apparatus Used)
a desk-top scanning electron microscope (manufactured by JEOL Ltd., JCM-6000Plus)
(Measuring Conditions)
acceleration voltage: 5.0 kV, magnification: 1000-power, pre-treatment: vapor deposited with gold microparticles

Figure 2:
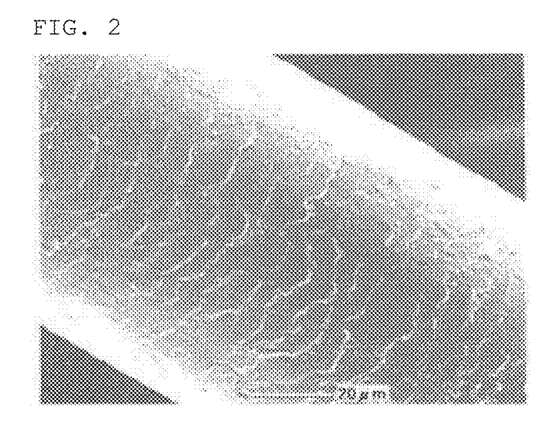
FIG. 2 is a photograph of an electron microscope image of the hair observed before the treatment in Example 43.
Figure 3:
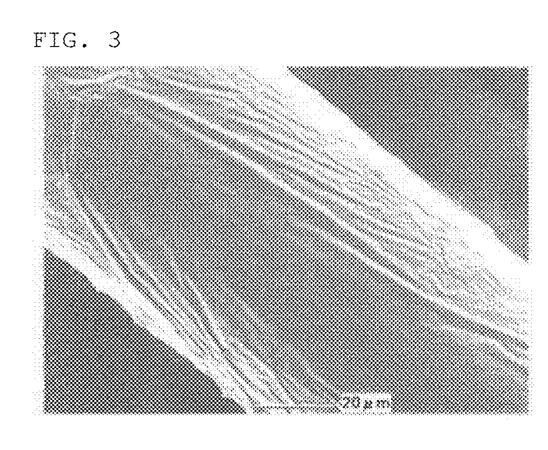
FIG. 3 is a photograph of an electron microscope image of the hair observed after the treatment in Example 43.
Figure 4:
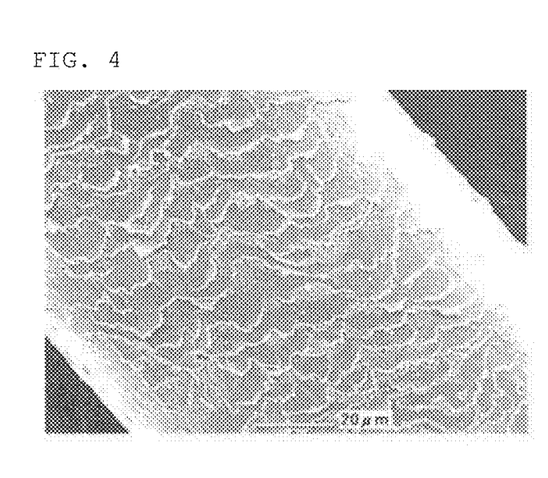
FIG. 4 is a photograph of an electron microscope image of the hair observed after a shampoo in Example 43.

The photographs of an electron microscope of the hair observed before the treatment, after the treatment, and after the shampoo are shown in FIG. 2 to FIG. 4 respectively. As a result, it was confirmed that the highly viscous polyether-modified silicone was stuck on the whole surface of the hair after treated with the hair protective agent, and was sufficiently removed from the surface of the hair after the shampoo without showing tendency to remain. Instead of washing with shampoo, the treated hair was introduced into a vessel containing water and was washed for 5 minutes with shaking. This was dried in the same manner as in the above, and then observed and photographed through an electron microscope. The hair was remained in the state with the whole surface being uniformly protected. This revealed that the emulsion composition described above forms a hair protective agent with excellent adhesion properties to hair, water resistance, and easiness of being removed with shampoo.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A bicontinuous microemulsion composition, comprising:
(A) polyglycerin group-containing organo(poly)siloxane shown by the following general formula (1):

wherein
each $R^1$ independently represents an alkyl group having 1 to 10 carbon atoms or a phenyl group,
$R^2$ represents a group having a polyglycerin structure shown by the following formula (2) or the following formula (3),
each $R^3$ independently represents $R^1$ or $R^2$,
"a" is a number of 0 to 6 and "b" is a number of 0 to 4 satisfying that a+b is 0 to 10, with the proviso that when "b" is 0, at least one of $R^3$ is $R^2$:

wherein
$R^4$ represents an alkylene group having 2 to 10 carbon atoms or an aralkylene group having 7 to 10 carbon atoms,
"c" is a number of 0 to 10, and "d" is a number of 2 to 6;
(B) at least one kind of oil selected from the group consisting of silicone oils having a viscosity of 20 mm$^2$/s or less at 25° C., volatile hydrocarbon oils, and ester oils; and
(C) water.

2. The bicontinuous microemulsion composition according to claim 1, wherein each $R^1$ in the general formula (1) independently represents an alkyl group having 1 to 5 carbon atoms in the (A) polyglycerin group-containing organo(poly)siloxane.

3. The bicontinuous microemulsion composition according to claim 2, wherein, in the (A) polyglycerin group-containing organo(poly)siloxane of the general formula (1),
$R^2$ is the same as described above,
$R^3$ is $R^1$,
"a" is a number of 0 to 2 and "b" is 1 satisfying that a+b is 1 to 3,
$R^4$ in the formulae (2) and (3) is the same as described above, and
the formula (2) is such that "c" is 0 and "d" is a number of 2 to 3; and
the bicontinuous microemulsion composition is oily.

4. The bicontinuous microemulsion composition according to claim 2, wherein, in the (A) polyglycerin group-containing organo(poly)siloxane of the general formula (1),
$R^2$ and $R^3$ are the same as described above,
at least one of $R^3$ is $R^2$,
"a" is a number of 2 to 6 and "b" is 0 satisfying that a+b is 2 to 6,
$R^4$ in the formulae (2) and (3) is the same as described above, and
the formula (2) is such that "c" is 0 and "d" is a number of 3 to 5; and
the bicontinuous microemulsion composition is oily.

5. The bicontinuous microemulsion composition according to claim 2, wherein, in the (A) polyglycerin group-containing organo(poly)siloxane of the general formula (1),
$R^2$ is a group shown by the formula (2),
$R^3$ is $R^1$,
"a" is a number of 0 to 1 and "b" is a number of 1 to 2 satisfying that a+b is 1 to 3, and
the formula (2) is such that $R^4$ is the same as described above,
"c" is 0, and
"d" is a number of 4 to 6; and
the bicontinuous microemulsion composition is aqueous.

6. The bicontinuous microemulsion composition according to claim 2, wherein, in the (A) polyglycerin group-containing organo(poly)siloxane of the general formula (1),
$R^2$ is a group shown by the formula (2),
$R^3$ is $R^1$,
"a" is a number of 0 to 2 and "b" is a number of 2 to 4 satisfying that a+b is 2 to 4, and
the formula (2) is such that $R^4$ is the same as described above,
"c" is 0, and
"d" is a number of 2 to 3; and
the bicontinuous microemulsion composition is aqueous.

7. The bicontinuous microemulsion composition according to claim 2, wherein, in the (A) polyglycerin group-containing organo(poly)siloxane of the general formula (1),
$R^2$ and $R^3$ are the same as described above,
at least one of $R^3$ is $R^2$,
"a" is a number of 0 to 1 and "b" is a number of 0 to 1 satisfying that a+b is 0 to 2,
$R^4$ in the formulae (2) and (3) is the same as described above, and
the formula (2) is such that "c" is 0 and "d" is a number of 3 to 6; and
the bicontinuous microemulsion composition is aqueous.

8. The bicontinuous microemulsion composition according to claim 2, wherein, in the (A) polyglycerin group-containing organo(poly)siloxane of the general formula (1),
$R^2$ and $R^3$ are the same as described above,
"a" is a number of 0 to 3 and "b" is a number of 0 to 3 satisfying that a+b is 0 to 6,
$R^4$ in the formulae (2) and (3) is the same as described above, and
the formula (2) is such that "c" is a number of 2 to 10 and "d" is a number of 2 to 6; and
the bicontinuous microemulsion composition is aqueous.

9. The bicontinuous microemulsion composition according to claim 1, wherein $R^1$ in the general formula (1) represents a methyl group in the (A) polyglycerin group-containing organo(poly)siloxane.

10. The bicontinuous microemulsion composition according to claim 1, wherein, in the (A) polyglycerin group-containing organo(poly)siloxane of the general formula (1),
each $R^3$ independently represents an alkyl group having 6 to 10 carbon atoms or a phenyl group,
$R^2$ is a group shown by the formula (2),
"a" is a number of 0 to 2 and "b" is a number of 2 to 4 satisfying that a+b is 2 to 4, and
the formula (2) is such that $R^4$ is the same as described above,
"c" is 0, and
"d" is a number of 2 to 3; and
the bicontinuous microemulsion composition is oily.

11. A cosmetic comprising the bicontinuous microemulsion composition according to claim 1.

12. A cosmetic comprising the bicontinuous microemulsion composition according to claim 2.

13. A cosmetic comprising the bicontinuous microemulsion composition according to claim 3.

14. A cosmetic comprising the bicontinuous microemulsion composition according to claim 4.

15. A cosmetic comprising the bicontinuous microemulsion composition according to claim 5.

16. A cosmetic comprising the bicontinuous microemulsion composition according to claim 6.

17. A cosmetic comprising the bicontinuous microemulsion composition according to claim 7.

18. A cosmetic comprising the bicontinuous microemulsion composition according to claim 8.

19. A cosmetic comprising the bicontinuous microemulsion composition according to claim 10.

20. The bicontinuous microemulsion composition according to claim 1, wherein the bicontinuous microemulsion composition does not contain water-soluble monovalent alcohol or polyvalent alcohol.

* * * * *